US011384950B2

(12) United States Patent
Nourbakhsh et al.

(10) Patent No.: US 11,384,950 B2
(45) Date of Patent: Jul. 12, 2022

(54) PROACTIVE BUILDING AIR QUALITY MANAGEMENT

(71) Applicant: Airviz Inc., Pittsburgh, PA (US)

(72) Inventors: Illah Nourbakhsh, Pittsburgh, PA (US); Dömötör Gulyás, Pittsburgh, PA (US); Chris Bartley, Pittsburgh, PA (US); Sara Longo, Pittsburgh, PA (US)

(73) Assignee: AIRVIZ INC., Pittsburgh, PA (US)

( * ) Notice: Subject to any disclaimer, the term of this patent is extended or adjusted under 35 U.S.C. 154(b) by 13 days.

(21) Appl. No.: 16/703,078

(22) Filed: Dec. 4, 2019

(65) Prior Publication Data

US 2020/0224915 A1   Jul. 16, 2020

Related U.S. Application Data

(60) Provisional application No. 62/793,094, filed on Jan. 16, 2019.

(51) Int. Cl.
| F24F 11/64 | (2018.01) |
| G01N 33/00 | (2006.01) |
| F24F 11/72 | (2018.01) |
| F24F 11/54 | (2018.01) |
| F24F 11/56 | (2018.01) |
| F24F 11/49 | (2018.01) |

(52) U.S. Cl.
CPC .............. *F24F 11/64* (2018.01); *F24F 11/49* (2018.01); *F24F 11/54* (2018.01); *F24F 11/56* (2018.01); *F24F 11/72* (2018.01); *G01N 33/0034* (2013.01); *G01N 33/0075* (2013.01)

(58) Field of Classification Search
CPC ...... F24F 11/64; F24F 11/54; G01N 33/0075; G01N 33/0034
See application file for complete search history.

(56) References Cited

U.S. PATENT DOCUMENTS

| 10,139,384 | B1* | 11/2018 | Nourbakhsh | ...... G01N 33/0062 |
| 10,222,360 | B1* | 3/2019 | Nourbakhsh | ...... G01N 33/0075 |
| 2013/0245837 | A1* | 9/2013 | Grohman | ............... H05B 47/11 700/276 |
| 2018/0073759 | A1* | 3/2018 | Zhang | ..................... G05B 17/02 |
| 2019/0346170 | A1* | 11/2019 | Benefield | ................ H04W 4/33 |
| 2019/0346417 | A1* | 11/2019 | Benefield | ................ H04W 4/38 |
| 2019/0360711 | A1* | 11/2019 | Sohn | ........................ F24F 11/80 |
| 2021/0342722 | A1* | 11/2021 | Han | ......................... G06N 3/08 |

* cited by examiner

Primary Examiner — Mohammad Ali
Assistant Examiner — Vincent W Chang
(74) Attorney, Agent, or Firm — K&L Gates LLP

(57) ABSTRACT

An air quality management system comprises a plurality of air quality sensors to sense air quality within a building, a plurality of air cleaning devices, and a computer system in communication with the plurality of air quality sensors and the plurality of air cleaning devices. The plurality of air quality sensors is located at a particular location within the building. The computer system determines a correlational model of air quality for the building that indicates a correlational relationship between the sensed air quality, a spatial parameter, a temporal parameter, and operation of the air cleaning devices. The computer system controls the plurality of air cleaning devices to implement an air quality control policy based on one or more air quality management parameters.

18 Claims, 2 Drawing Sheets

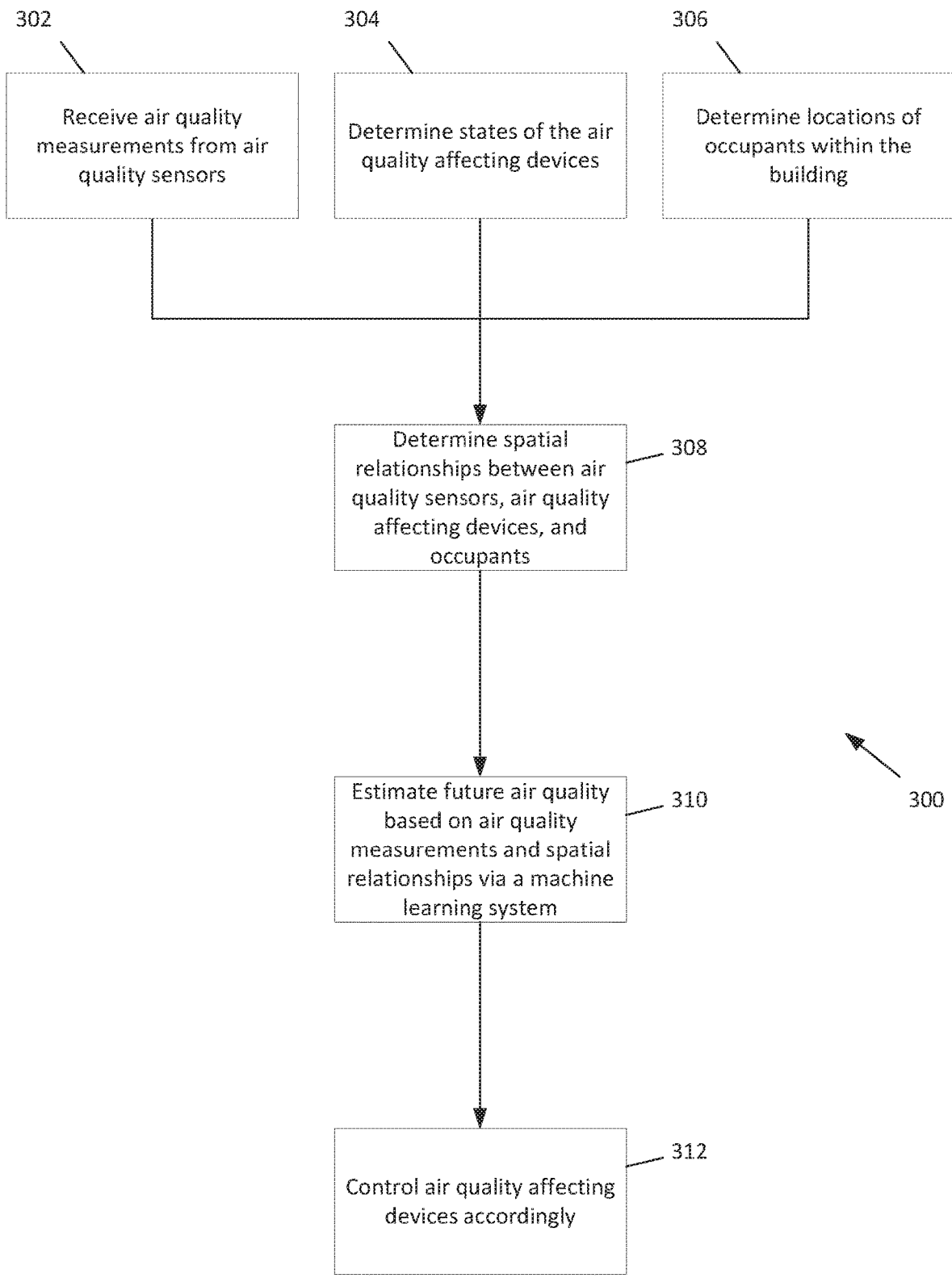

PROACTIVE BUILDING AIR QUALITY MANAGEMENT

PRIORITY

This application claims priority under 35 U.S.C. § 119(e) to U.S. provisional patent application No. 62/793,094, titled PROACTIVE BUILDING AIR QUALITY MANAGEMENT, filed Jan. 16, 2019, which is hereby incorporated by reference herein in its entirety.

FIELD OF INVENTION

The present invention relates to control systems that manage the air quality in a building based on sensing air quality measures and other air quality-related measures. As such, an understanding of the causal relationship between independent events and controllable actions with respect to air quality is achieved. This relationship may be used proactively to improve and to maintain good air quality in the building, at both a general level and at specific sub-regions of the interior spaces of the building.

BACKGROUND

Significant bodies of research indicate that cumulative, personal exposure to fine particulates (i.e., $PM_{2.5}$) is strongly correlated with pulmonary disease and cardiovascular disease. See, e.g., U.S. Pat. No. 8,147,302. In addition, statistically significant correlations exist between exposure to $PM_{2.5}$ by pregnant women and the onset of autism and attention deficit hyperactivity disorder in children. Thus, for both personal health and the health of progeny, the active reduction of cumulative personal air pollution exposure carries significant value in mitigating the risks of pulmonary disease, cardiac disease, asthma, and numerous infant health concerns. For individuals, significant proportions of exposure to air pollution derive from time spent inside buildings, such as during eating and nighttime sleep.

Conventional approaches to maintaining the best possible air quality in indoor spaces are fragmentary. Some approaches involve the measurement of indoor air quality. For instance, it is known to use networked air quality sensors in homes to create unique fingerprints for each resident for characterizing each home's air quality. However, such systems fail to actively improve air quality. In particular, conventional whole-house HVAC filters remove particulates from the home when HVAC systems' fans are operational, but conventional systems do not proactively control HVAC fan speed based on air quality. Existing room air purifiers include purifiers that filter a single room's air in manual operation or in response to a low-cost dust-measuring optical sensor. However, these systems are both inaccurate and reactive, not predictive and proactive. That is, they are only able to act once the air quality has already deteriorated significantly, providing limited value in maintaining clear air for occupants.

SUMMARY

In one general aspect, the present invention is directed to an air quality management system that operates based on creating a model of human behavior and of causal links between actions within the home (or another building) and effects on air quality. In this way, such a model directly represents how actions or conditions within the building change or cause other effects on air quality in the building. Some causal links would enable proactive purification of the air as particulates are disturbed or generated, which significantly increases the responsiveness of the present air quality management system. The present invention considers both air pollution and air cleaning actions at the hyper-local level within a building. Air quality management at this resolution may advantageously avoid premature overuse of air filters, energetic inefficiency, and broad nonspecific targeting of air filters. In this way, the present invention may enhance the ability to focus air pollution amelioration actions at the precise location of building occupants, which can maximize system efficacy. As such, embodiments of the present invention overcome some of the disadvantages of conventional systems. These and other benefits realizable with the present invention will be apparent from the description below.

BRIEF DESCRIPTION OF THE FIGURES

Various embodiments of the present invention are described herein by way of example in conjunction with the following figure, wherein:

FIG. 2 is a logic flow diagram of a process for managing the air quality in a building according to various embodiments of the present invention.

DETAILED DESCRIPTION

Figure 1:
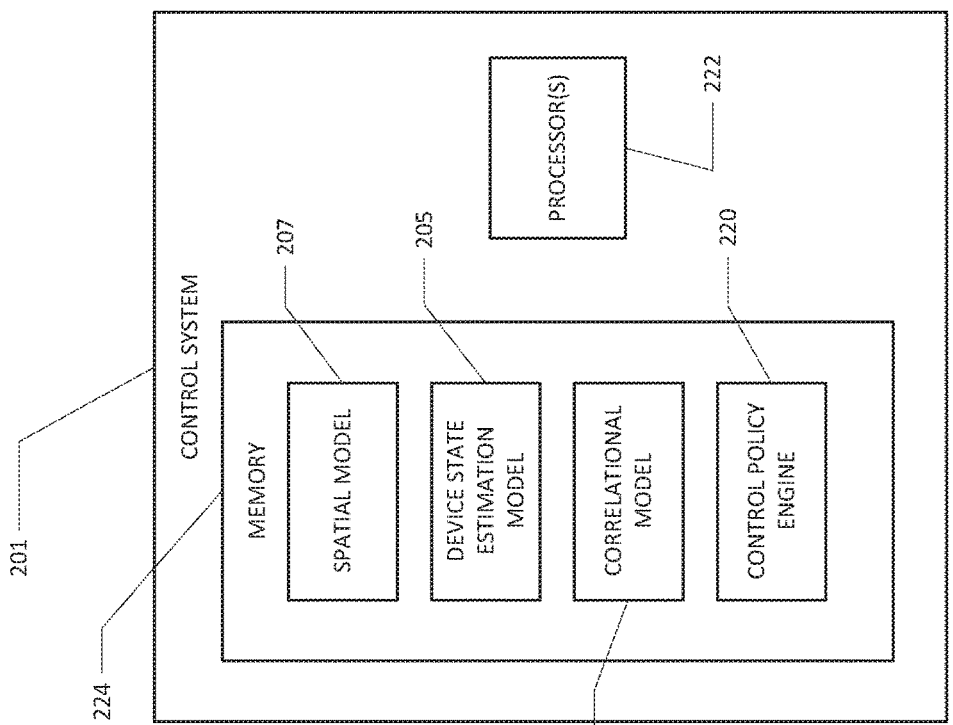
FIG. 1 is a block diagram of a proactive air quality control system according to various embodiments of the present invention.
Figure 1:
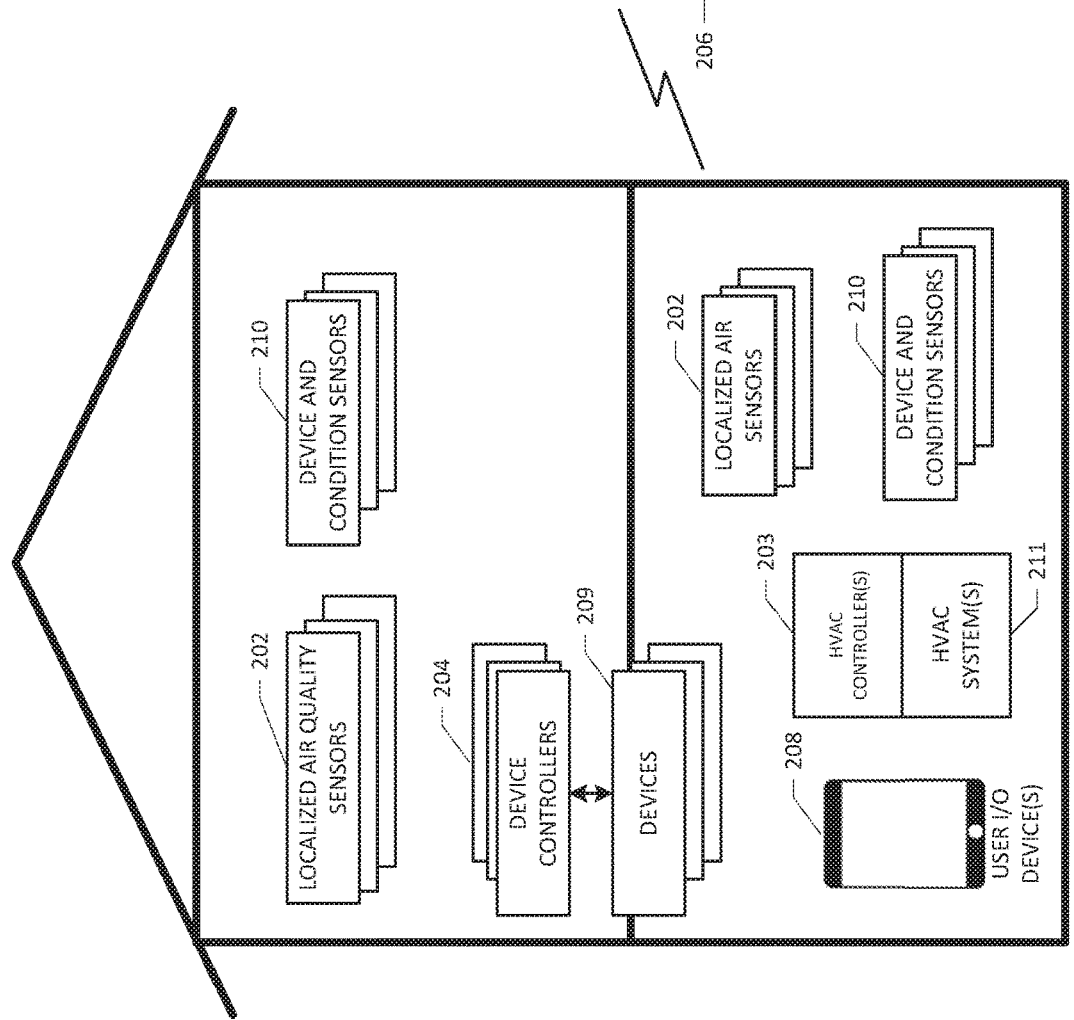

The following description has set forth aspects of computer-implemented devices and/or processes via the use of block diagrams, flowcharts, and/or examples, which may contain one or more functions and/or operations. As used herein, the terms "model," "engine," and "step" in reference to the block diagrams and flowcharts refers to a step of a computer-implemented process executed by a computer system. Each model, engine, and/or step can be implemented as either a machine learning system or as a nonmachine learning system, according to the function described in association with each particular model, engine, and/or step. Furthermore, each model, engine, and/or step can refer to one of multiple steps of a process embodied by computer-implemented instructions executed by a computer system (which may include, in whole or in part, a machine learning system) or an individual computer system (which may include, e.g., a machine learning system) executing the described step, which is in turn connected with other computer systems (which may include, e.g., additional machine learning systems) for executing the overarching process described in connection with each figure or figures. Accordingly, the model, engine, and/or step can refer to the action and processes of a computer system e.g., the control system 201 of FIG. 1, or similar electronic computing device, that manipulates and transforms data represented as physical (electronic) quantities within the computer system's registers and memories into other data similarly represented as physical quantities within the computer system memories or registers or other such information storage, transmission or display devices.

The present invention, in one general aspect, is directed to a system that implements proactive air quality control in a building via the confluence of multiple components, including: sensors for low-cost, high-precision air quality sensing; communications infrastructure for low-barrier communication between Internet-of-Things (IoT) devices within the building; active air quality control throughout a structure;

data storage, machine learning, and classification for characterization of causal links between actions, events, measurements, and air quality; and active fine-grained abilities to control air purification devices over digital communication pathways. The system can proactively manage building air quality across three major categories of activity: discovery, control, and diagnosis. The discovery category includes determining correlational relationships between various air quality related actions (e.g., purifying air in the building with an air filter) with sensed air quality at precise times and spatial location within the building. The control category includes proactively using the determined correlational relationships to implement an air quality management optimization function. The diagnosis category includes continuously using the control system to continuously perform diagnostic analysis of whole-system efficacy and isolated subsystem performance of the building air quality architecture.

With reference now to FIG. 1, there is shown a proactive air quality control system for a building. In the following description of FIG. 1, reference should also be made to FIG. 2. In various embodiments, localized air quality sensors 202 can be are placed in particular rooms and/or locations in the building. Each location may define a spatial zone within the building, for example. The air quality sensors 202 described herein can be any suitable "smart" air quality sensor that can report its readings to a remote or local control system 201, as shown in FIG. 1. The air quality sensor can comprise, for example, an optical particle sensor that uses a laser or LED(s). One such air quality sensor is described in U.S. Pat. No. 9,857,301, which is hereby incorporated by reference in its entirety. The air quality sensors 202 can continuously generate time-stamped air quality measurements in real time, which may be reported to and stored by the control system 201. International patent application publication no. WO 2017/204866, which is hereby incorporated by reference in its entirety, provides more details about generation and storage of such time-stamped sensor readings.

Referring to the example embodiment shown in FIG. 1, various numbers of air quality sensors 202 are placed in specific rooms or locations in the building to provide real-time air quality measurements with high spatial resolution. The building may be, for example, a house, an apartment building, an office building, a manufacturing plant, a warehouse, an arena, a bus or airport terminal, a hotel/motel, or any other type of building where air quality for occupants is important. In the case of a house, for example, an air quality sensor in a child's bedroom in the building/house would provide real-time information regarding air quality with high spatial resolution for that bedroom. The spatial resolution and location can be determined by a back-end computer-based control system 201 (comprising suitable amounts of processors and memory devices), which could be located at the building or remote from the building (e.g., in a cloud computing system). Additionally or alternatively, the selected spatial resolution and location for the air quality sensors could be input to the control system 201 or otherwise selected/specified by the user via a user I/O device 208 that communicates with the control system 201. For example, the user may decide that there should be three different spatial zones within the building (e.g., kitchen, living room, and bedroom; or first floor, second floor, and basement). This could be useful because different spatial zones may have different correlational or causal relationships between activities (e.g., cooking by residents of the building), times, and air quality trends. Incorporating a greater level of spatial granularity may enable the control system 201 to determine a better correlation model and better implement proactive air quality control.

For determination of spatial zones, the control system 201 may initially determine the spatial location of a first air quality sensor 202 located in the building and determine other spatial locations of the remaining air quality sensors 202 in the building using a suitable technique, such as evaluating location based on relative received signal strength (RSSI) and/or traversing a mesh network, for example. Also, the user could instead manually describe the spatial locations by inputting this information via the user I/O device 208, which may be a smartphone, a tablet, a laptop, or any other computer type device that communicates with the control system 201. The manual description by the user might address situations where RSSI is not strong enough.

The air quality sensors 202 may be communicatively coupled to the control system 201 (back-end computer system). The control system 201 may also be in communication with multiple other devices that affect and/or report data indicative of air quality in the building. Such other devices may include a HVAC controller(s) 203 that controls the HVAC system(s) 211 for the building or sub-region(s) of the building. The HVAC system(s) 211 could also include active baffling and sub-region controls that can be controlled by the HVAC controller(s) 203, and hence by the control system 201 through communication with the HVAC controller(s) 203. The other devices may also include air quality-relevant devices 209 and/or their corresponding controllers 204. The devices 209 may affect air quality, either negatively or positively, and include devices such as in-room air purifiers, air filters, kitchen hood vents, automatic window and blind/curtain controls, kitchen devices, laundry, or other appliances, etc.

Such other devices 209 may also comprise device or condition sensors 210 that sense whether certain devices are on in the building (and if on, their operating condition if appropriate) and/or whether certain conditions are present in the building. Such sensors 210 may generate outputs indicative of device conditions, including whether the vacuum cleaner is running (and where in the building), whether a fireplace is on, whether the stove or oven is on, whether a humidifier or dehumidifier is running, whether gas is detected (e.g., via carbon monoxide sensors), or whether a fire or smoke is detected. These sensors 210 may be direct or indirect sensors. For example, the devices 209 could include a gas fireplace that may have a sensor 210 that monitors the on/off switch and reports the condition of the gas fireplace to the control system 201. An indirect fireplace sensor may sense that the fireplace is on based on inputs from a thermometer, a thermal imaging sensor, a microphone (for the sound of the fan of the fireplace), and/or a camera, for example.

Based on diverse means for communication, synchronization of pairing of local air quality sensors and local means of air cleaning may occur. This can constitute a spatial registry of sensing and direct action locales throughout the building. One example direct action locale could be a portion of the living room of the building, where several large automatically openable windows are located. The spatial registry can be used in conjunction with whole-building geometric modeling. The whole-building geometric modeling may include models for whole-building air cleaning devices, such as the whole building HVAC air purification system, and local air cleaning devices, such as local air quality purification means.

Various device and condition sensors 210 (aside from the air quality sensors 202) digitally connected to the computer-based control system 201 may be used to measure or track the timing of air quality-relevant actions taking place in the home. These actions may be mapped to the temporal information monitored by the control system 201. Such devices 210 can include motion sensors, device status indicators, and other suitable devices. The motion sensors and/or other device and condition sensors 210 can be used to identify and monitor human activity in the building, for example. In this way, the device and condition sensors 210 in combination with the control system 201 can identify periods of high amounts of walking/movement or other activity throughout the building (which could correspond to higher amounts of pollution when humans are present in the building and engaged in some air pollution generating activity) or low periods (no humans are present). Furthermore, device status indicators can communicate to the control system 201 to indicate when other air quality-relevant actions are occurring, such as vacuum cleaner use, robotic vacuum cleaner action, clothes dryer operation, and the like. The air quality-relevant actions can be manual, automatic, or a combination of both. In general, the control system 201 may use the timing of these actions, the spatial geometry of the building, and the corresponding measured air quality from the air quality sensors 202 to proactively control the multiple devices 209 (e.g., air cleaning devices) within the building to proactively improve the air quality of the building. In this way, as described in further detail below, the control system 201 can generate a correlational model 206 of air quality that incorporates temporal causal relations between activities, times, and air quality trends.

With the derived correlational model 206, the control system 201 may actively control systems of the building to minimize air pollution exposure for building occupants. The optimization control policy may operate based on multiple variables of optimization, including occupant exposure, system noise/quality of experience for occupants, energy use, filter deterioration rates, etc. The multiple optimization variables could be expressed in a utility function applied by the control system 201, as described in further detail below. The control system 201 may be communicatively coupled to as many (spatially) diverse air quality sensors 202 and other building state and activity information fluents (e.g., from data sources such as the device/condition sensors 210) as required. In general, the control system 201 may use the derived correlational model 206 for discovery, control, and diagnosis. Many different types of proactive control could be achieved by the control system, including controlling air filter/purifiers, HVAC, robotic devices, and robotic controllers. The proactive control may be based on combining a diverse collection of information, a correlational temporal model of events, controls and air quality trends, and proactive control to optimize air quality under a multi-parametric rubric (e.g., optimization variables). For example, the control system 201 could activate an air cleaning device on a high fan speed cleaning setting in a bedroom of the building. The monitored temporal information could be used by the control system 201 to determine that the high-speed cleaning occurs before occupant nighttime entry to prepare the bedroom for clean-air maintenance during sleeping hours while minimizing noise exposure.

The control system 201 may also proactively start HVAC fan operation when a smoke/CO/gas sensor (which could be one of the device and condition sensors 210) detects high levels of pollution trending upwards. Additionally, if a smoke/CO/gas alarm is detected, the proactive starting of the HVAC fan may be overridden. In another example, temporal and spatial aspects of the correlational model 206 may be used to time an air cleaning action controlled by the control system 201 to proactively address expected air pollution. In one specific example, the computer-based control system 201 can activate fan-only operation of the building HVAC system 211 in concert with active baffles control to focus cleaning energy on the bedroom directly above the kitchen, in synchrony with kitchen hood vent operation, to proactively avoid particulate exposure of the bedroom. By timing these air cleaning actions in this way, this may avoid a situation in which a nearby bedroom is pervaded with cooking particles. The correlational model 206 may also be used to proactively target locations within the building when expected peaks in air pollution are occurring. Thus, the control system 201 may proactively transmit a request to a robotic device 209 or device controller 204 (e.g., a robotic air cleaning device, such as a robotic mobile vacuum or a robotic air purifier, in a specific room of the building) to activate when the peak pollution is expected. In this way, the air cleaning devices 209 corresponding to a specific building region are activated and begin cleaning to reduce the local air particulate peaks for the specific region.

This control process may also involve the control system 201 communicating with device controllers 204 for the air quality-relevant devices 209 (e.g., devices whose operation impacts air quality such as air cleaning devices) or communicating directly with the air quality-relevant devices 209. For example, the control system 201 could communicate with the device controller 204 for multiple robotically controlled open/close building windows (which could be one or more of the devices 209) so that the control system 201 transmits a request to the device controller 204 to open the associated window of a room prior to that room experiencing high air pollution. Similarly, the control system 201 could communicate with the device controller for robotic air cleaners 209 such that the spatial location with peak pollution can be cleaned by the activated corresponding device 209. The control system 201 can preemptively indirectly or directly control air cleaning devices 209 for other reasons, such as actions by humans in the building. For example, if a human occupant begins vacuuming, the control system 201 may cause active robotic opening of windows in the vicinity of the vacuuming because it is expected that indoor air pollution is likely to increase and exceed outdoor air pollution in the vicinity of the vacuuming.

This expectation can be validated by the control system 201 by receiving estimates/predictions of outdoor air quality (and temperature, humidity, etc.) from federal sensors and weather centers, for example. Further, the accuracy of these estimates could be improved by the local sensors 202 placed around the exterior of the building. Also, the device/condition sensors 210 may be provided to determine the corresponding device state of the various air quality-relevant devices or air-quality conditions in the building. These device/condition sensors 210 could be local/integrated with the device(s) 209 or device controller(s) 204, or they may be located remotely. As such, the device/condition sensors 210 may directly or indirectly sense the state of the devices 209. For example, a machine-learning system could indirectly learn when the vacuum cleaner is running based on sound picked up by a microphone, motion sensors detecting movement of the vacuum cleaner, heat sensors sensing heat from the vacuum cleaner's motor, video images from a camera, and/or voltage drops on the building electrical system. Alternatively, the vacuum cleaner could have an IoT sensor that directly reports its state, such as to the control system 201. Various direct or indirect sensors could be used for various other devices that affect air quality as described herein, such as fireplaces, fans, vents, ovens, stoves, other appliances, windows and blinds, fire and carbon monoxide sensors, etc. The device/condition sensors 210 may be communicatively coupled to the control system 201 to send data about what they have sensed so that the control system 201 may determine the state of the device and/or conditions related to the air quality, for example (fireplace on or off, fan on or off, vacuum cleaner on or off, etc.). The device data received by the control system 201 could also be used in the device state estimation model 205. Device states may include on/off state, power level, operational parameters such as baffling state, and other suitable states.

Similarly, the control system 201 could cause windows to be robotically closed when it is determined that a neighbor of the building is engaged in air quality-relevant activities that would negatively affect air quality, such as cutting the grass, burning leaves, etc. Such situations may be detected with the temporal information of the correlational model 206, such as determining that it is an appropriate time for the neighbor to cut the grass based on how tall the grass is and the last time the grass was cut. Also, a machine-learning system could be trained to sense the neighbor mowing the yard based on distinctive sound profiles indicative of a lawn mower captured by a microphone near the neighbor's yard. Additionally or alternatively, other sensors 210 (e.g., olfactory sensors) could be coupled to the control system and provide outputs indicating such air quality-relevant activities are occurring. More specifically, the building may have air quality sensors 202 strategically placed in local outdoor locations around the building perimeter. In this way, the control system 201 can cause active closure of windows when local outdoor air quality sensors generate output data that demonstrate localized poor air quality. For example, when a neighbor is using an outdoor wood-burning home heating system, the windows to proximal areas in the building that would be effected can be closed. These examples illustrate that the whole-building system described herein can provide localized, proactive protection for building occupants at a high level of efficacy.

Moreover, in order to maximize efficacy over time, the control system 201 can further perform diagnostic analysis of whole-system efficacy and isolated subsystem performance continuously. As such, the control system 201 may diagnose the effect or estimated effect of air cleaning devices and/or air quality-relevant devices 209 or actions. For example, multiple techniques within the purview of individual room-air purifiers may enable estimation of the efficacy of each such unit, based on distributed air quality sensing information and correlation tables already created. Indirect measurements of filter deterioration, spanning from motor current sensing and optical filter life estimation to direct measurements of flow or pressure drop within the air purifier body provide evidence of efficacy locally. Automatic diagnostic analysis enables the system to provide explicit recommendations to building management or occupants, including, for example, the replacement of specific filters, the cleaning of specific air ducts, attention to service for particular devices such as a vacuum cleaner or kitchen hood vent, etc. These actions could also be incorporated as part of the control functionality of the control system 201, such as the control system 201 sending a signal to the device controller 204 for a group of air filter devices 209 such that an appropriate one of the group is replaced when that filter has exceeded its effective working life, for example.

FIG. 1 is a block diagram of a proactive air quality control system for a building according to various embodiments of the present invention. The block diagram of FIG. 1 comprises the computer control system 201, the localized air quality sensors 202, the HVAC controller(s) 203 for controlling associated HVAC systems 211, the device controller(s) 204 for controlling associated devices 209, and the device/condition sensors 210. These devices, along with a user's I/O device(s) 208, may be, directly or indirectly, in communication with the control system 201, which may be local to or remote from the building.

The control system 201 may be implemented with one or a number of networked computer devices, such as servers, PCs, mainframes, etc. Where multiple computer devices are used, they may be co-located or distributed, such as via a LAN, WAN, the Internet, etc. The control system 201 is programmed to generate a device state estimation model 205, a correlational model 206, and a spatial model 207. The control system 201 can further be programmed to implement a control policy engine 220 to control the air quality affecting devices 209, which can include the HVAC system(s) 211, according to the outputs of the models 205, 206, 207. The device state estimation model 205, correlational model 206, spatial model 207, and/or control policy engine 220 can be stored in a memory 224 of the control system 201 such that they can be executed by processor(s) 222 coupled to the memory 224. The control system 201 represents the processing center of the air quality management system. In particular, the control system 201 receives the inputs from the various system components 202, 203, 204, 208, 210, etc., transmits outputs to other system components (e.g., device controllers 204 and HVAC controllers 203), and derives and executes, according to various embodiments, optimizing control policies to maximize or enhance chosen utility functions for building performance in order to effect low air pollution exposure for building occupants. The localized air quality sensors 202 may provide real-time air quality values to the control system 201, which may be time-stamped and stored in a database of the control system 201 for historical analysis. The control system 201 may be communicatively coupled to each of the other components of the system shown in FIG. 1 via any suitable communication link, such as via a direct connection (e.g., Ethernet) or a wireless connection such as Bluetooth (e.g., Bluetooth Low Energy) or WiFi.

In one embodiment, the local air quality sensors 202 provide timestamped, direct air quality readings indicative of $PM_{2.5}$ particulate load values to the control system 201. Moreover, the control system 201 may further comprise an online repository or database for storing the timestamped air quality sensor readings. The timestamped readings may comprise a variety of measurements, including: size-bucketed particulate concentrations, mass concentrations, volatile organic compound (VOC) readings, CO and CO2 readings, temperature and humidity readings, and other measures of air quality with high relevance to human health and comfort. From the sensed air quality measurements, as well as data from the other devices 209, the control system 201 can control the other air quality management subsystems in the building (e.g., HVAC systems, windows, vents, fans) to implement the selected control policy. For example, communication with the HVAC controllers 203 can enable the control system 201 to directly control device settings. For example, the control system 201 can set whether a HVAC system 211 is on or off, whether it is heating or cooling (if on), its power level (e.g., high or low power level), and whether its fan is on/off and the fan's power level, and/or an appropriate combination or subcombination of the above. Additionally, the fan power level and other operational parameters besides on/off could be controlled by the control system 201 based on spatial, temporal, and other air quality-relevant information. The HVAC controllers 203 could also communicate cooling and heating states relative to A/C cooling and heating usage to the control system 201.

The HVAC systems 211 may have baffles or other guidance systems/methods to guide or alter the flow of air throughout the HVAC system 211, which may be controlled by the HVAC controllers 203. In such situations, the HVAC controller 203 could directly control, in response to commands from the control system 201, the baffles or other means for redirecting air of the HVAC systems 211 in localized ways to target precise air cleaning operations based on the correlational model 206, for example. Any suitable such pathway of communication between IoT devices is possible. Thus, the HVAC controller 203 may provide HVAC state information to the control system 201, which in turn may redirect and/or restrict air flow as required according to the determined control policy. The HVAC state may be controlled based on the derived correlational model 206 such that when human occupants are residing in a room of the building for long periods of time, for example, the HVAC fan is set to circulate air for ~10 minutes per hour. This can be achieved by a smart HVAC controller 203.

HVAC controllers 203 that are digitally enabled can provide direct interfaces for effecting control of the building HVAC system(s) 211. While the HVAC system(s) 211 can be whole-building, they may also be fractional, part-building systems. HVAC controllers 203 may include control of heating and air conditioning, as well as nonheated and nonconditioned fan-only operation suitable for drawing air through centralized HVAC air filters even when temperature modifications to the built environment are not required. The multiple modes of operation may be controlled according to the HVAC controller's 203 own control algorithm, as well as by the control system 201 according to the applied air quality control policy. To this end, the HVAC controllers 203 can provide state information regarding their operational characteristics to the control system in real time, including whether they are on or off, fan speed information, and heating/cooling state information, as well as expected downtimes for scheduled maintenance and dynamic operational limits.

The device controllers 204 also can provide informational data to the control system 201 for analysis as discussed in further detail herein. Also, they may optionally present interfaces and affordances for direct control of the air quality-relevant devices 209 to which they are linked. Preferably, devices 209, such as room air purifiers, used individually throughout the building are able to be remotely activated by the control system 201 through their corresponding device controllers 204. In addition, semi-autonomous room-air purifiers can provide state information regarding fan speed and dust sensor readings digitally to the control system 201. As a result, device controllers 204 for diverse air quality-relevant devices 209 effect notification of state to control system 201. Where the air quality-relevant devices 209 have semi-autonomous operability, they may share some or all of the control otherwise exerted by control system 201.

Examples of air quality-relevant devices 209 with digitally connected device controllers 204 include, but are not limited to: room air purifiers, room-cleaning robots, digitally connected kitchen hood vents, digitally connected robotic window openers, digitally connected vacuum cleaners, digitally connected clothes dryers, motion sensors, smart home thermostat controllers, smart home I/O appliances, etc. These devices 209 also can be capable of automatic or manual control, as noted above. Accordingly, automatic control devices could include digitally controllable kitchen hood vents or autonomously steered robotic vacuum cleaners, for example. Exclusively manually controlled but digitally connected devices 209 could be connected vacuum cleaners, clothes dryers, and manual windows, for example. Device controllers 204 and sensors 210 that provide passive state information or active control interfaces afford the control system 201 the opportunity to annotate system state for the various devices and the opportunity to explicitly activate and deactivate digitally controllable devices 209. Because all these exemplified devices 209 have direct impact on air quality, the ability to measure and manipulate their state represent important degrees of information and control freedom for the control system 201 to proactively model and optimize building air quality.

The control system 201, as shown in FIG. 1, generates a device state estimation model 205, a spatial model 207, and a correlation model 206, which are described further herein. Based on these models, a control policy engine 220 can implement a desired control policy for the building. In that connection, based on determinations by the control policy engine 220, the control system 201 can transmit control commands to various devices 209, 211 and/or device controllers 203, 204 in the building to positively control the air quality in the building, such as described herein.

The control system 201 is programmed to generate a device state estimation model 205 for the devices 209 coupled to respective device controllers 204 and for the HVAC system(s) 211. Additionally or alternatively, the control system 201 may receive data indicative of device state indirectly from the corresponding device controller 204 (coupled to one or more device 209) or directly via the sensors 210. Device state may include on/off state, power level, operational parameters such as baffling state, and other suitable states. By combining incoming state information from all of the plurality of device controllers 203, 204 and/or air quality-relevant devices 211, 209 in the building, the control system 201 can update and maintain state information regarding all accessible or measurable devices 211, 209. In addition to automatically receiving state information from device controllers 204 and HVAC controller 203, the control system 201 may receive manually entered information as well. Manual entry may occur through a user I/O device, such as mobile user I/O device 208. The device state estimation model 205 can include historical and present state of all measurable and observable device states relevant to building air quality and may be stored in a database or repository of the control system 201.

Preferably, state values include a significant variety of timestamped informational fluents. Such information fluents could also be spatially annotated or locationally stamped. Examples of fluents include: room air purifier states (e.g., fan speed, dust sensor reading, filter installation date, room air purifier air pressure value, motor back-EMF current value), fireplace state, window position, dryer mode, vacuum cleaner mode, autonomous robotic vacuum cleaner mode, HVAC states (e.g., HVAC-measured temperatures, HVAC mode and fan speed, HVAC filter installation date, filter life estimation, HVAC system active baffling state), kitchen hood fan speed, dishwasher states, oven and stovetop states, all air quality sensor 202 readings throughout the building (inside and outside), and human occupancy readings (including who, which room(s), etc.). In cases of partially observable or noisy data, the control system 201 may employ a Kalman filter to generate the device state estimation model 205 to reduce noise while tracking system state accurately. In the case of nonlinear noise, an extended Kalman filter could be used in order to maximize accuracy of state estimation.

Using the state information (e.g., information fluents), the control system 201 also, through appropriate programming, builds and maintains a spatial model 207 showing the spatial relationship between physical devices 209, 211, air quality sensor(s) 202, occupants within the building, and various other tracked parameters having a spatial component. For example, when the state information indicates that an air purifier is on at certain time periods, and a particular air quality sensor 202 shows improved air quality for those same time periods, the control system 201 can determine for purposes of the spatial model that the air purifier and air quality sensor are near each other. In a similar manner, the spatial relationship between other devices 209, 211 and sensors 210 can be determined. Additional data about the spatial relationships for the spatial model 207 can be provided directly by a user via a user I/O device 208. For example, the user could specify, via an appropriate interface provided by the I/O device 208 (e.g., an app including a graphical user interface), that a particular air sensor 202 and a particular air purifier device 209 are co-located in a particular room or that another particular air quality sensor 202 is co-located in another particular room with a fireplace device 209.

The control system 201 can also be programmed to track real-time human occupancy of the building and/or the rooms/locations thereof. Real-time human occupancy can be tracked with sensors 210, such as motion sensors, door sensors, and/or cameras. For example, the net number of people in a building or on a floor can be tracked by tracking ingress and egress through doors. Human occupancy can also be tracked for particular humans by tracking the location of mobile devices associated with the particular humans, such as their smartphones, smart watches, tablets, mobile devices, etc. For example, if person A's mobile device connects to a WiFi router in room Y, the spatial model 207 can determine that person A is near room Y. Similarly, if person B's mobile device connects via BLE to a BLE device in room Z, the spatial model 207 can determine that person B is near room Z. Also, other presence sensors/systems, such as contactless smart cards, light switches, or appliance usage, could be used to estimate general locations of individuals in the building. For example, if a sensor 210 senses water running in a shower, the spatial model 207 can estimate that a person is in a bathroom; if a person swipes their smart card to enter a location in a building, the spatial model 207 can estimate that the person is in the corresponding location of the building; or if kitchen appliances are being used, the spatial model 207 can assume that the kitchen is occupied. The spatial model 207 could also use geofencing to estimate the number and identity people in the building or locations thereof. To that end, the identity of specific people can influence the applied control policy. If a person known to frequent the building is known to suffer from chronic obstructive pulmonary disease, the control policy engine 220 of the control system 201 can cause an air purifier device in the person's room to operate at desired power levels when the spatial model 207 detects that the person is in or near their room. Therefore, using geofencing or other location/presence technology, the control system 201 may be aware of building occupancy, enabling identity-based air cleaning.

Using temporal (and spatial) correlational analysis, the control system 201 uses the device state estimation model 205 (device state over time) and the spatial model 207 to build, refine, and maintain a correlational model 206 that estimates correlations between all measurable information fluents, temporal schedules, and air quality at variable resolution throughout the building. That is, the correlational model 206 can represent causal relations between activities, times, and air quality trends in a temporal and spatial manner. As one example, the correlational model 206 can incorporate or be implemented as a Dynamic Bayesian Network that relates all device states and air quality states over time and establishes correlational strength links between all such variable states. In particular, the correlational model 206 may be implemented as a multilayer recurrent neural network that estimates air quality over tactical time based on device states as inputs. This recurrent neural network enables the capture of temporal delay and hysteresis while maximizing the future-facing predictive power of the correlational model 206. In this way, the correlational model 206 establishes/represents likely future air quality based on observable parameters, such as human occupancy, human manual actions, cooking events, purifier fan settings, environmental conditions, and others.

The spatial model 207 represents the correlational and geometric distance between actionable control system outputs. For all possible outputs of the control system 201 to device controllers 204, 203, the spatial model 207 establishes the causal likelihood of the actions' impact on air quality sensor readings. Actions can be, for example, turning on an air purifier device 209 located in the room above the kitchen to a high fan speed. Also, these outputs can be digitally set. As one example, the spatial model 207 can incorporated or be implemented as a Dynamic Bayesian Network prepopulated with geometric proximity information to establish strong lines of influence between specific device actions and proximal sensors. Establishment of positional proximity to specific device actions may be performed through multiple spatial reasoning processes, including: (1) human map annotation and map modification using the user I/O device 208 to identify the building architecture, as well as the location of devices 209 and sensors 202, 210; (2) proximity-based auto-discovery for the control system 201 to seed, improve, and evolve spatial proximity information; (3) whole-building geolocation services provided through mixed GPS and in-building WiFi-based indoor GPS services; (4) gesture-based human confirmation of proximity, including the tapping of a mobile user I/O device 208 on proximal air quality-relevant devices 209 in succession, such as tapping an air quality in-room sensor and an in-room air purifier; and (5) explicit BLE pairing of proximal devices 209. The auto-discovery could be achieved by first identifying an air quality device and traversing through a mesh network of air quality-relevant devices 209, 202, 210 in the building. Proximity information can be derived from digital radio signal strength, including BLE and WiFi, which can be measured by RSSI.

Using the correlational model 206 to estimate future states based on possible controllable device outputs, and using the spatial model 207 to search the space of possible output actions to minimize poor air quality exposure for building occupants, the control system 201 implements a control policy engine 220 with both reactive control strategies to maximize utility and strategic, schedule-based default strategies to maximize utility. In other words, based on the correlational model 206 and spatial model 207, the control policy engine 220 can implement a desired proactive air quality control policy. The control policy may be defined by desired optimization variables, which form a utility function. A schedule-based approach of the control system 201 can enable utility maximization for ritual, repeating events, such as pre-cleaning a bedroom at the correct initial start time to ensure low noise and clean air during bedtime. Meanwhile, the reactive approach of the control system 201 resolves a search of real-time actions that yield strictly improved utility function responses in the near future.

In one aspect, the utility function optimized by the control system 201 can be represented as a linear utility function of the form:

$$u(X_1, X_2, \ldots, X_m) = W_1 X_1 + W_2 X_2 + \ldots W_m X_m$$

Here, u is the utility function. Each variable x represents a state variable with correspondence to overall utility as explained herein. Each weight w is adjusted to ensure that air pollution exposure is minimized for the building occupants but only while maintaining constraints/bounds on energy use, filter degradation, and noise pollution. The constraints may include air quality device operational constraints, constraints imposed by the user, and other suitable constraints. The optimization variables x may include: $PM_{2.5}$ occupant exposure, total joules of energy consumed, building $PM_{2.5}$ mean value, temperature variation from desired set point, and aggregate filter degradation slope.

Control parameters that the control policy engine 220 may also use in determining actions to take may include optimization variables, such as cost and energy consumed by devices of the building. For example, between two alternatives that improve air quality in approximately the same amount, the control policy engine 220 can implement the one that costs less and/or consumes less energy. For example, it may be just as effective, but less expensive and less energy consuming, to open a specifically located window for a period of time than to turn on multiple high power fans, but with approximately the same air quality effect. In that case, the optimization calculation by the control policy engine can determine that the window should be opened instead of turning on the multiple high power fans.

Additionally, a user may have input to the control policy implemented by the control policy engine 220. For example, via the user I/O device 208, the user may adjust control parameters for the control policy. In other words, the user could select or change optimization variables or constraints applied by the control policy engine 220. For example, the user, via I/O device 208, could set a maximum amount of kilowatt-hour (kWh) consumed by devices 209, 211, a maximum amount of x ppm of air pollution, etc. Further, the control system 201 can transmit notifications to the user I/O device 208 with real-time instructions or recommendations that the user can implement to improve building air quality, such as manually closing and opening of manual doors or windows, turning on or off devices that the control system 201 cannot control directly, replacement or servicing of air filters and air quality-impinging devices in the building, etc. In various embodiments, the user may input queries to the control system 201 via I/O device 208 for suggestions on actions to take for addressing air quality, such as the real-time instructions or recommendations described above.

The user I/O interface 208 may enable the control system 201 to expose the user to control strategy, including scheduled air quality control parameters. For example, the user could set a series of targeted air quality measurements that each should be reached in a certain amount of time. In this connection, the control system 201 may also effectively perform real-time diagnostics that provide diagnostic, actionable recommendations to the user. System diagnostics include: measures of changes in the efficacy of air filters in reducing measured air pollution, tracking changes in the correlational model 206 weights over time, the measured efficacy of individual devices (whose device controllers 204 provide diagnostically useful data to the control system 201). Diagnostic or operational parameter data of air quality-relevant devices may include: ambient to loaded pressure drops inside room air purifier vessels when their fans are activated, back-EMF motor current sensing to indirectly measure air filter throughput efficiency, and flow meter values from purifiers to directly measure air throughout. In all such cases, changes to direct and indirect efficiency values prompt the control system to provide notification to the user I/O device 208. These notifications can be triggered when the efficiency value or other tracked parameter exceeds a corresponding control limit or threshold. Thus, for example, the control system 201 may identify needed repairs and replacement activities of various devices or other components to return the air quality system to nominal working condition.

In one general aspect, therefore, the present invention is directed to an air quality control system comprising a plurality of air quality sensors 202 to sense air quality within a building, a plurality of device and building conditions sensors 210, a plurality of air cleaning (or otherwise air affecting) devices 203, 204, 209, 211, and a computer-based control system 201 in communication with system components (devices/sensors). The control system 201 determines a correlational model 206 of air quality for the building that indicates a correlational relationship between the sensed air quality, a spatial parameter, a temporal parameter, and operation of the air cleaning (or otherwise air-affecting) devices. The control system 201 controls the plurality of air cleaning devices to implement an air quality control policy based on one or more air quality management parameters. A remote user I/O device 208 can be used to define one or more air quality management parameters.

Accordingly, a computer system, such as the control system 201 illustrated in FIG. 1, can execute the process 300 illustrated in FIG. 2 to manage the air quality in a building. The process 300 can be embodied as computer executable instructions stored in a memory 224 of the control system 201, such that, when executed by processor(s) 222 coupled to the memory 224, the instructions cause the control system 201 to perform the enumerated steps.

At a first step 302, the control system 201 executing the process 300 can receive air quality measurements from the air quality sensors 202. At a second step 304, the control system 201 can determine the states or conditions of the air quality affecting devices 209 (e.g., whether a device 209 is activated, the power level of a device 209, or the operational mode of a device 209). As described above, the states of the air quality affecting devices 209 can be determined in a number of different manners, including by receiving the states directly from the devices 209 themselves, receiving the states from device controllers 204 coupled to the devices 209, by sensing the states via device/condition sensors 210 configured to indirectly sense the state/condition of a device 209 (e.g., a camera, thermometer, or microphone configured to sense whether a fireplace is activated), and so on. The states of the air quality affecting devices 209 can be represented by a device state estimation model 205, which is described above and can be stored in the memory 224 of the control system 201. At a third step 306, the control system 201 can determine locations of occupants within the building. As described above, the device/condition sensors 210 can include motion sensors, cameras, and other sensors configured to detect and track the movement of occupants throughout the building. Accordingly, the control system 201 can determine the occupants' locations by receiving images and/or sensor readings from such sensors.

At a fourth step 308, the control system 201 can determine spatial relationships between the air quality sensors 202, the air quality affecting devices 209 (which can also include the HVAC system(s) 211), and the occupants. The locations of the physical devices (i.e., the air quality sensors 202, air quality affecting devices 209, HVAC system(s) 211, and so on) and/or occupants can be sensed or determined by the control system 201 (e.g., by sensing the locations of occupants via motion sensors or sensing physical devices locations based on RSSI and/or traversing a mesh network), received from the physical devices themselves, or manually input by a user (e.g., via a smartphone app). The locations of the sensors 202, devices 209, and/or occupants can be represented by a spatial model 207, which is described above and can be stored in the memory 224 of the control system 201.

At a fifth step 310, the control system 201 can estimate the future air quality of the building and/or regions thereof based on the received air quality measurements and the spatial relationships of the air quality sensors 202, air quality affecting devices 209, and occupants via a machine learning system. In one implementation, the machine learning system can be trained (e.g., using training data via supervised or unsupervised machine learning techniques) to correlate device states and air quality states over time to future air quality metrics. The machine learning system can include or be embodied by a correlational model 206, which is described above and can be stored in the memory 224 of the control system 201.

At a sixth step 312, the control system 201 can control the air quality affecting devices 209 according to the estimated future air quality (e.g., in order to mitigate an expected poor future air quality). The control system 201 can implement a set of rules or algorithms that are programmed to define the manner in which the various air quality devices 209 are controlled by the control system 201 based on the estimated future air quality. Such rules could include opening a window in a room when a fireplace in that room is activated, starting the HVAC system 211 and opening the baffles of an air return in the kitchen when stovetop burners are activated, and so on. The manner in which the air quality affecting devices 209 are controlled by the control system 201 can be established by a control policy engine 220, which is described above and can be stored in the memory 224 of the control system 201.

With respect to the described processes (e.g., the process 300), those skilled in the art will appreciate that recited operations therein may generally be performed in any order, unless explicitly described otherwise. Also, although various operational flow diagrams are presented in a sequence(s) and/or particular steps are described numerically (e.g., a "first step" and a "second step"), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory (e.g., the memory 224) in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "processor" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The processor may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "processor" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The examples presented herein are intended to illustrate potential and specific implementations of the present invention. It can be appreciated that the examples are intended primarily for purposes of illustration of the invention for those skilled in the art. No particular aspect or aspects of the examples are necessarily intended to limit the scope of the present invention. Further, it is to be understood that the figures and descriptions of the present invention have been simplified to illustrate elements that are relevant for a clear understanding of the present invention, while eliminating, for purposes of clarity, other elements. While various embodiments have been described herein, it should be apparent that various modifications, alterations, and adaptations to those embodiments may occur to persons skilled in the art with attainment of at least some of the advantages. The disclosed embodiments are therefore intended to include all such modifications, alterations, and adaptations without departing from the scope of the embodiments as set forth herein.

What is claimed is:

1. An air quality control system for a building, the air quality control system comprising:
    a plurality of air quality sensors to sense air quality and located at different locations within the building;
    one or more occupancy sensors;
    a plurality of air quality affecting devices comprising:
        a first set of one or more air quality affecting devices that positively affect air quality; and
        a second set of one or more air quality affecting devices that negatively affect air quality;
    a plurality of device sensors, each of the plurality of device sensors associated with one or more of the plurality of air quality affecting devices; and
    a computer system in communication with the plurality of air quality sensors and the plurality of air quality affecting devices, the computer system comprising:
        a processor; and
        a memory coupled to the processor, the memory storing instructions that, when executed by the processor, cause the computer system to, on an ongoing basis:
            receive air quality measurements from the plurality of air quality sensors;
            determine device states of the plurality of air quality affecting devices from sensor data from the plurality of device sensors;
            determine spatial locations of the plurality of air quality sensors based on received signal strengths of wireless signals from the plurality of air quality sensors;
            determine, based on the one or more occupancy sensors, locations of occupants in the building;
            maintain a spatial model that indicates spatial relationships between the plurality of air quality sensors, the plurality of air-quality affecting devices, and occupants of the building;
            predict a future air quality of the building based upon the received air quality measurements and the determined spatial relationships by, through machine learning, determining a correlation of the device states of the plurality of air quality affecting devices to future air quality; and
            control the air quality affecting devices to affect air quality in the building according to the predicted future air quality.

2. The air quality control system of claim 1, wherein the first set of one or more air quality affecting devices that positively affect air quality comprises an air cleaning device.

3. The air quality control system of claim 2, wherein the first set of one or more plurality of air quality affecting devices that negatively affect air quality comprises an air contaminating device.

4. The air quality control system of claim 1, wherein the plurality of device sensors comprise a device sensor that is configured to receive a first device state of an air quality affecting device from a device controller associated with the air quality affecting device, wherein the first device state comprises on/off state, power level, and/or operational parameters.

5. The air quality control system of claim 1, wherein the plurality of device sensors comprise a device sensor that is integrated into an air quality affecting device.

6. The air quality control system of claim 1, wherein the plurality of device sensors comprise a device sensor that is configured to sense a first device state of an air quality affecting device based on measurements of the air quality affecting device, wherein the first device state comprises on/off state, power level, and/or operational parameters.

7. The air quality control system of claim 1, wherein the computer uses a recurrent neural network trained to predict the future air quality of the building based upon the received air quality measurements and the determined spatial relationships as inputs thereto.

8. The air quality control system of claim 1, wherein:
    the first set of one or more air quality affecting devices that negatively affect air quality comprises an air quality affecting device selected from the group consisting of a window, a fireplace, a kitchen device, an appliance, a vacuum, and a door; and
    the first set of one or more air quality affecting devices that positively affect air quality comprises an air quality affecting device selected from the group consisting of an air purifier, an air filter, a fan, and an HVAC system.

9. A back-end computer system for controlling air quality of a building, the back-end computer system comprising:
    a processor; and
    a memory coupled to the processor, the memory storing instructions that, when executed by the processor, cause the computer system to, on an ongoing basis:
        receive air quality measurements from a plurality of air quality sensors associated with the building;
        receive occupancy information from one or more occupancy sensors associated with the building;
        determine device states of a plurality of air quality affecting devices associated with the building from sensor data from a plurality of device sensors associated with a plurality of air quality affecting devices, wherein the plurality of air quality affecting devices comprises:
  a first set of one of more air quality affecting devices that positively affect air quality; and
  a second set of one or more air quality affecting devices that negatively affect air quality;
determine spatial locations of the plurality of air quality sensors based on received signal strengths of wireless signals from the plurality of air quality sensors;
determine, based on the one or more occupancy sensors, locations of occupants in the building;
maintain a spatial model that indicates spatial relationships between the plurality of air quality sensors, the plurality of air-quality affecting devices, and occupants of the building;
predict a future air quality of the building based upon the received air quality measurements and the determined spatial relationships by, through machine learning, determining a correlation of the device states of the plurality of air quality affecting devices to future air quality; and
control the air quality affecting devices to affect air quality in the building according to the predicted future air quality.

10. A computer-implemented method for controlling air quality of a building, the method comprising:
  receiving, by a computer system, air quality measurements from a plurality of air quality sensors associated with the building;
  receiving, by one or more occupancy sensor, occupancy information associated with the building;
  determining, by the computer system, device states of a plurality of air quality affecting devices associated with the building from sensor data from a plurality of device sensors associated with a plurality of air quality affecting devices, wherein the plurality of air quality affecting devices comprises:
    a first set of one of more air quality affecting devices that positively affect air quality; and
    a second set of one or more air quality affecting devices that negatively affect air quality;
  determine spatial locations of the plurality of air quality sensors based on received signal strengths of wireless signals from the plurality of air quality sensors;
  determine, based on the one or more occupancy sensors, locations of occupants in the building;
  maintaining, by the computer system, a spatial model that indicates spatial relationships between the plurality of air quality sensors, the plurality of air-quality affecting devices, and occupants of the building;
  predicting, by the computer system, a future air quality of the building based upon the received air quality measurements and the determined spatial relationships by, through machine learning, determining a correlation of the device states of the plurality of air quality affecting devices to future air quality; and
  controlling, by the computer system, the air quality affecting devices to affect air quality in the building according to the predicted future air quality.

11. The computer-implemented method of claim 10, wherein the first set of one or more plurality of air quality affecting devices that positively affect air quality comprises an air cleaning device.

12. The computer-implemented method of claim 11, wherein the first set of one or more plurality of air quality affecting devices that negatively affect air quality comprises an air contaminating device.

13. The computer-implemented method of claim 10, wherein the plurality of device sensors comprise a device sensor that is configured to receive a first device state of an air quality affecting device from a device controller associated with the air quality affecting device, wherein the first device state comprises on/off state, power level, and/or operational parameters.

14. The computer-implemented method of claim 10, wherein the plurality of device sensors comprise a device sensor that is integrated into an air quality affecting device.

15. The computer-implemented method of claim 10, wherein the plurality of device sensors comprise a device sensor that is configured to sense a first device state of an air quality affecting device based on measurements of the air quality affecting device, wherein the first device state comprises on/off state, power level, and/or operational parameters.

16. The computer-implemented method of claim 10, wherein predicting the future air quality through machine-learning system comprises using a recurrent neural network that is trained to predict the future air quality of the building based upon the received air quality measurements and the determined spatial relationships as inputs thereto.

17. The computer-implemented method of claim 10, wherein:
  the first set of one or more air quality affecting devices that negatively affect air quality comprises an air quality affecting device selected from the group consisting of a window, a fireplace, a kitchen device, an appliance, a vacuum, and a door; and
  the first set of one or more air quality affecting devices that positively affect air quality comprises an air quality affecting device selected from the group consisting of an air purifier, an air filter, a fan, and an HVAC system.

18. The computer-implemented method of claim 10, further comprising:
  sensing, by the plurality of air quality sensors, the air quality measurements, wherein each of the plurality of air quality sensors is located at a different location within the building and each of the plurality of air quality sensors is in communication with the computer system;
  sensing, by the plurality of device sensors, the states of the plurality of air quality affecting devices, wherein each of the plurality of devices sensors are in communication with the computer system; and
  sensing, by the computer system, locations of the occupants of the building via one or more motion sensors.

* * * * *